US00PP20417P2

(12) United States Plant Patent
Bergman

(10) Patent No.: US PP20,417 P2
(45) Date of Patent: Oct. 13, 2009

(54) *HIBISCUS* PLANT NAMED 'PIPEDREAM TANGERINE'

(50) Latin Name: *Hibiscus rosa-sinensis*
Varietal Denomination: Pipedream Tangerine

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/221,685

(22) Filed: Aug. 4, 2008

(51) Int. Cl.
*A01H 5/00* (2006.01)

(52) U.S. Cl. ..... Plt./257
(58) Field of Classification Search ..... Plt./257
See application file for complete search history.

*Primary Examiner*—Kent L Bell
(74) *Attorney, Agent, or Firm*—C. A. Whealy

(57) ABSTRACT

A new and distinct cultivar of *Hibiscus* plant named 'Pipedream Tangerine', characterized by its compact, upright, somewhat outwardly spreading, uniformly rounded and dense plant habit that is appropriate for container production; glossy dark green-colored leaves; uniform, freely and early flowering habit; large bright yellow-colored flowers with orange and pink-colored centers; and good postproduction and garden performance.

1 Drawing Sheet

Botanical designation: *Hibiscus rosa-sinensis.*
Cultivar denomination: 'Pipedream Tangerine'.

BACKGROUND OF THE INVENTION

The present invention relates to a new and distinct cultivar of *Hibiscus,* botanically known as *Hibiscus rosa-sinensis,* and hereinafter referred to by the name 'Pipedream Tangerine'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good garden performance.

The new *Hibiscus* originated from a cross-pollination made by the Inventor in Alva, Fla. in February, 2004, of a proprietary selection of *Hibiscus rosa-sinensis* identified as code number YB-2449, not patented, as the female, or seed, parent with a proprietary selection of *Hibiscus rosa-sinensis* identified as code number YB-2310, not patented, as the male, or pollen, parent. The new *Hibiscus* was discovered and selected by the Inventor as a flowering plant within the progeny of the stated cross-pollination in a controlled greenhouse environment in Alva, Fla. on Sep. 12, 2005.

Asexual reproduction of the new *Hibiscus* by vegetative terminal cuttings in a controlled greenhouse environment in Alva, Fla. since February, 2006, has shown that the unique features of this new *Hibiscus* are stable and reproduced true to type in successive generations.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pipedream Tangerine'. These characteristics in combination distinguish 'Pipedream Tangerine' as a new and distinct cultivar of *Hibiscus:*

1. Compact, upright, somewhat outwardly spreading, uniformly rounded and dense plant habit that is appropriate for container production.
2. Glossy dark green-colored leaves.
3. Uniform, freely and early flowering habit.
4. Large bright yellow-colored flowers with orange and pink-colored centers.
5. Good postproduction and garden performance.

Plants of the new *Hibiscus* can be compared to plants of the female parent selection. Plants of the new *Hibiscus* differ from plants of the female parent selection in the following characteristics:

1. Plant of the new *Hibiscus* have larger flowers than plants of the female parent selection.
2. Plants of the new *Hibiscus* have flowers with more substance than plants of the female parent selection.
3. Plants of the new *Hibiscus* and the female parent selection differ in flower color as plants of the female parent selection have yellow-colored flowers with orange-colored centers.

Plants of the new *Hibiscus* can be compared to plants of the male parent selection. Plants of the new *Hibiscus* differ from plants of the male parent selection in the following characteristics:

1. Plants of the new *Hibiscus* are more robust than plants of the male parent selection.
2. Plants of the new *Hibiscus* and the male parent selection differ in flower color as plants of the male parent selection have light golden yellow-colored flowers with pink-colored centers.
3. Plants of the new *Hibiscus* have better garden performance than plants of the male parent selection.

Plants of the new *Hibiscus* can be compared to plants of the *Hibiscus rosa-sinensis* 'YOHIB 2362', disclosed in U.S. Plant Pat. No. 17,623. In side-by-side comparisons conducted in Alva, Fla., plants of the new *Hibiscus* differed from plants of 'YOHIB 2362' in the following characteristics:

1. Plants of the new *Hibiscus* had lighter green-colored leaves than plants of 'YOHIB 2362'.
2. Flowers of plants of the new *Hibiscus* and 'YOHIB 2362' differed in flower color as plants of 'YOHIB 2362' had yellow-colored flowers with red-colored centers.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph at the bottom of the sheet comprises a side perspective view of typical flowering plants of 'Pipedream Tangerine' grown in a container.

The photograph at the top of the sheet comprises a close-up view of a typical flower of 'Pipedream Tangerine'.

DETAILED BOTANICAL DESCRIPTION

The aforementioned photographs and following observations, measurements and values describe plants grown in Alva, Fla. in 15-cm containers in polycarbonate-covered greenhouses during the summer under conditions which closely approximate commercial production. During the production of the plants, day temperatures ranged from about 35° C. to about 38° C. and night temperatures ranged from about 20° C. to about 21° C. Plants had been growing for 15 weeks when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Pipedream Tangerine'.

Parentage:

*Female, or seed, parent.*—Proprietary selection of *Hibiscus rosa-sinensis* identified as code number YB-2449, not patented.

*Male or pollen parent.*—Proprietary selection of *Hibiscus rosa-sinensis* identified as code number YB-2310, not patented.

Propagation:

*Type.*—By vegetative terminal cuttings.

*Time to initiate roots.*—About 10 days at temperatures of 24° C.

*Time to develop roots.*—About four weeks at temperatures of 24° C.

*Root description.*—Thick, fibrous; white in color.

*Rooting habit.*—Moderate branching; moderately dense.

Plant description:

*Plant form and growth habit.*—Perennial, evergreen, upright, somewhat outwardly spreading, compact, uniformly rounded and dense. Moderately vigorous growth habit.

*Branching habit.*—Freely branching, usually about six lateral branches develop.

*Plant height.*—About 23 cm.

*Plant diameter* (*area of spread*).—About 30 cm.

Lateral branch description:

*Length.*—About 21 cm.

*Diameter.*—About 6 mm.

*Internode length.*—About 1.4 cm.

*Texture.*—Immature, smooth; mature, woody and rough.

*Color, immature.*—Close to N137B.

*Color, mature.*—Close to 199B to 199C.

Foliage description:

*Arrangement.*—Alternate, single; numerous; symmetrical.

*Length.*—About 9 cm.

*Width.*—About 7.3 cm.

*Shape.*—Ovate.

*Apex.*—Acute.

*Base.*—Cordate.

*Margin.*—Crenate; sinnuate.

*Texture, upper surface.*—Smooth, glabrous.

*Texture, lower surface.*—Pubescence along veins.

*Luster, upper surface.*—Glossy.

*Luster, lower surface.*—Somewhat glossy.

*Venation pattern.*—Pinnate; arcuate.

*Color.*—Developing leaves, upper surface: Close to 146A. Developing leaves, lower surface: Close to 146B. Fully expanded leaves, upper surface: Close to 139A; venation, close to 137A. Fully expanded leaves, lower surface: Close to 137B; venation, close to 146C.

*Petiole.*—Length: About 2.6 cm. Diameter: About 2.5 mm. Texture, upper and lower surfaces: Pubescent. Color, upper and lower surfaces: Close to 147A.

Flower description:

*Flower arrangement.*—Flowers arranged singly at terminal leaf axils. Uniform and freely flowering habit with usually about 14 flower buds and/or open flowers per plant at one time. Flowers face upright to outwardly.

*Flower appearance.*—Rounded, bright yellow-colored flowers with orange and pink-colored centers. Flowers are open for about two days. Flowers not persistent.

*Natural flowering season.*—Usually spring and summer or during periods of warm weather; plants flower year-round in the greenhouse.

*Flower diameter.*—About 8 cm.

*Flower length* (*height*).—About 6.2 cm.

*Flower bud.*—Resistance to abscission during shipping: Plants of the new *Hibiscus* have been observed to resist flower bud drop when stored in a closed box for five days at 13° C. Rate of opening: About five days depending on temperatures. Length: About 4.3 cm. Diameter: About 1.9 cm. Shape: Elliptic. Color: Close to 145B.

*Petals.*—Arrangement: Corolla consists of five petals that are fused at base; petals imbricate. Length: About 6 cm. Width: About 5.2 cm. Shape: Obovate. Apex: Rounded; slightly sinnuate. Base: Attenuate. Margin: Entire; slightly sinuate. Texture: Smooth, glabrous; velvety; veins prominent on the lower surface. Color: When opening, upper surface: Close to 13C. When opening, lower surface: Close to 10C. Fully opened, upper surface: Close to 13B; midsection, close to 23B to 23C; towards the center, close to 53A to 53B. Color does not fade with development. Fully opened, lower surface: Close to 11B; towards the base, close to 11D. Color does not fade with development.

*Sepals.*—Appearance: Five sepals fused into a tubular star-shaped calyx. Length: About 1.4 cm. Width: About 1.1 cm. Shape: Elliptical. Apex: Acute. Margin: Entire. Texture, upper surface: Smooth, glabrous. Texture, lower surface: Pubescent. Color, upper surface: Close to 146B. Color, lower surface: Close to 146A.

*Bracts.*—Appearance: About seven to nine fused at base. Length: About 1.7 cm. Width: About 4 mm. Shape: Lanceolate. Apex: Acute. Margin: Entire. Texture, upper surface: Smooth, glabrous. Texture, lower surface: Sparsely pubescent. Color, upper and lower surfaces: Close to 146B.

*Peduncles.*—Length: About 6 cm. Diameter: About 2 mm. Angle: About 45° from the lateral branch axis. Strength: Strong, flexible. Texture: Sparsely pubescent. Color: Close to 146A.

*Reproductive organs.*—Androecium: Stamen number: Numerous, about 96. Filament length: About 3.5 mm. Filament color: Close to 155D. Anther shape: Oval. Anther length: About 1 mm. Anther color: Close to 16A. Amount of pollen: Moderate. Pollen color: Close to 17A. Gynoecium: Pistil length: About 6.5 cm. Style length: About 5.2 cm. Style texture: Smooth, waxy. Style color: Close to 11B to 11C. Stigma appearance: Five-parted, rounded. Stigma color: Close to 15B. Ovary color: Close to 11C.

*Seed/fruit.*—Seed and fruit production has not been observed.

Garden performance: Plants of the new *Hibiscus* have been observed to have good garden performance and to tolerate wind, rain and temperatures from about 0° C. to about 38° C.

Pathogen/pest resistance: Plants of the new *Hibiscus* grown under Florida production conditions have not been shown to be susceptible to pathogens common to *Hibiscus* such as Pseudomonas, Pythium and Phytophthora. Plants of the new *Hibiscus* have not been observed to be tolerant to pests and other pathogens.

It is claimed:

1. A new and distinct *Hibiscus* plant named 'Pipedream Tangerine' as illustrated and described.

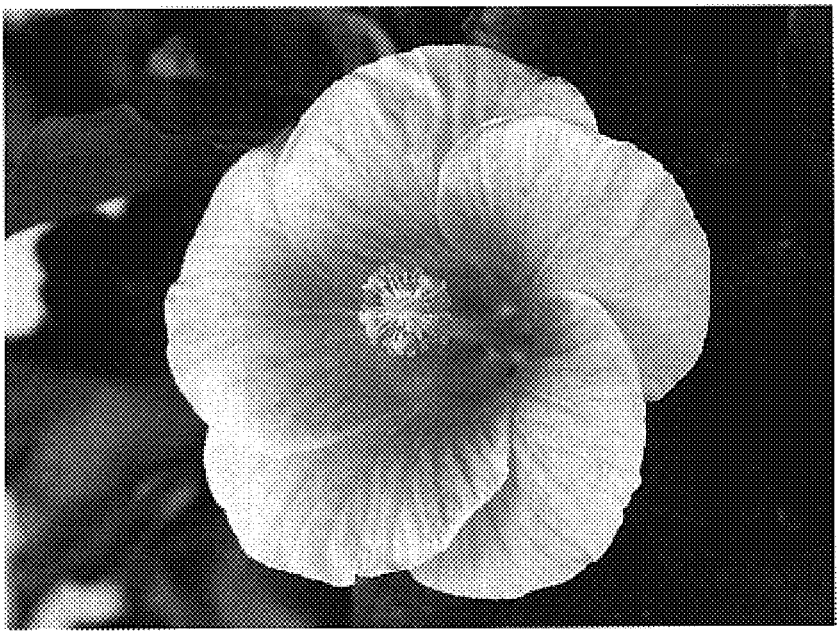
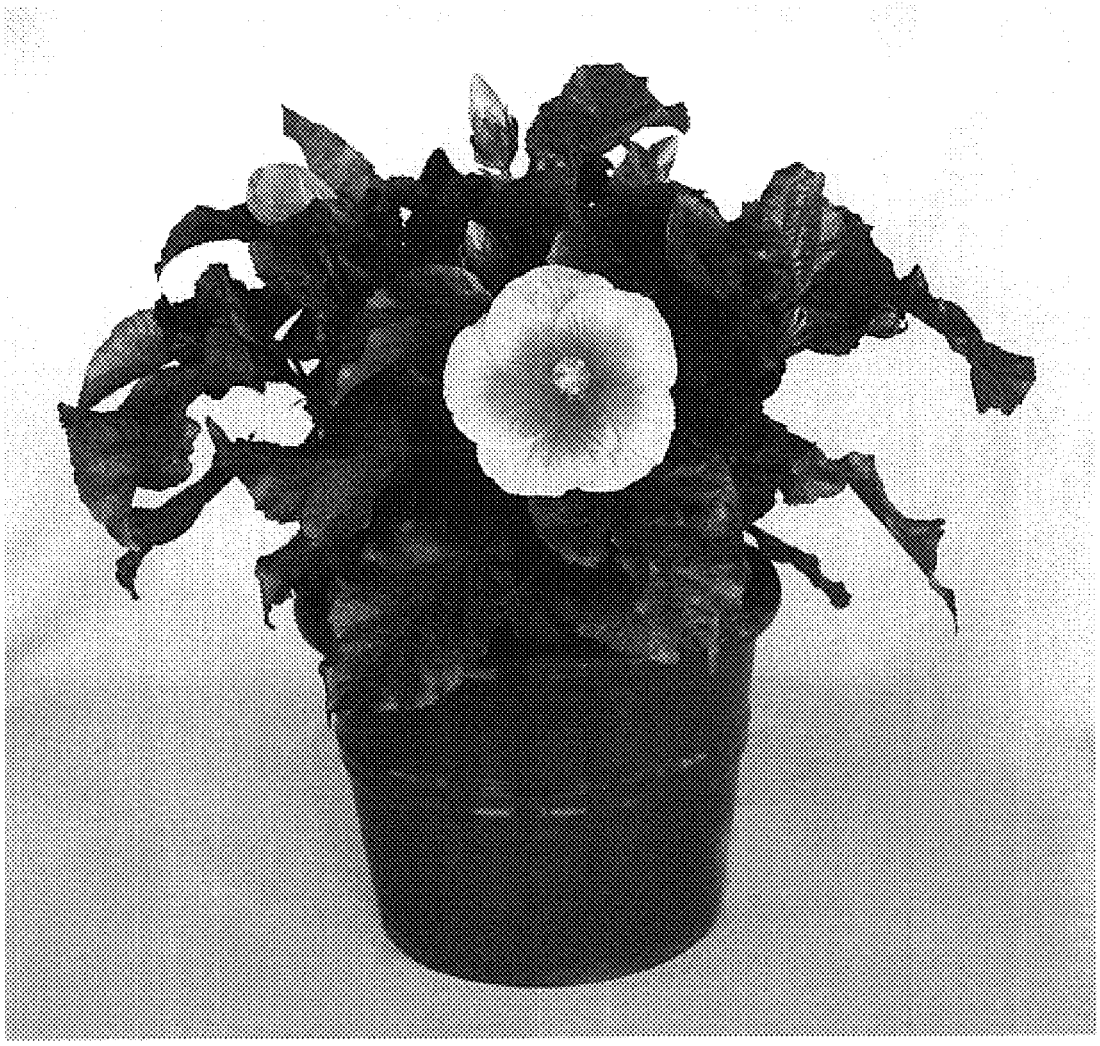

* * * * *